United States Patent [19]
VanBeek et al.

[11] Patent Number: 4,863,469
[45] Date of Patent: Sep. 5, 1989

[54] METHOD AND APPARATUS FOR EXPANDING NERVE TISSUE

[75] Inventors: Allen L. VanBeek, Edina; Alfred A. Iversen, Wayzata; William J. Eastman, St. Louis Park, all of Minn.

[73] Assignee: PMT Corporation, Chanhassen, Minn.

[21] Appl. No.: 110,407

[22] Filed: Oct. 20, 1987

[51] Int. Cl.[4] ............................................. A61F 2/12
[52] U.S. Cl. ....................................................... 623/8
[58] Field of Search ................. 128/325, 344; 623/8; 604/96-103

[56] References Cited

U.S. PATENT DOCUMENTS

| | | | |
|---|---|---|---|
| 3,480,013 | 11/1969 | Garber | 128/325 |
| 3,675,656 | 7/1972 | Hakim | 128/325 |
| 4,190,040 | 2/1980 | Schulte | 623/8 |
| 4,338,941 | 7/1982 | Payton | 128/325 |
| 4,574,780 | 3/1986 | Manders | 623/8 |
| 4,643,733 | 2/1987 | Becker | 623/8 |
| 4,666,447 | 5/1987 | Smith et al. | 623/8 |
| 4,685,447 | 8/1987 | Iversen et al. | 623/8 |
| 4,719,918 | 1/1988 | Bonomo et al. | 128/344 |
| 4,738,657 | 4/1988 | Hancock et al. | 623/8 |

Primary Examiner—John D. Yasko
Attorney, Agent, or Firm—Hugh D. Jaeger

[57] ABSTRACT

A nerve expander used in plastic reconstruction surgery for lengthening damaged nerves which facilitates reattachment of damaged nerves to facilitate nerve operation and function after reconstruction. One or more saddles on an inflatable expansion member positionally accommodates a nerve in a saddle trough. The nerve expander with the saddle mounted nerve is subsequently inflated with saline solution injected into a self-sealing injection port causing the inflatable expansion member to expand and the nerve thereabout to be stretched and lengthened.

3 Claims, 7 Drawing Sheets

METHOD AND APPARATUS FOR EXPANDING NERVE TISSUE

BACKGROUND OF THE INVENTION

1. Field of the Invention

The present invention relates to an inflatable nerve expander, and more particularly, pertains to a saddle on an inflatable nerve expander for positional accommodation and lengthening of a nerve for reattachment.

2. Description of the Prior Art

Prior art devices consisted chiefly of nerve expanders placed under a nerve for purposes of nerve expansion. Upon expansion of the nerve expander, the nerve placed over the nerve expander would often disengage itself from the position over the nerve expander, and slide off of the expander rendering the procedure useless until the nerve was replaced on top of the nerve expander again causing an undue waste of surgery time, effort and energy during the reconstructive process.

The present invention overcomes the disadvantages of the prior art by providing a nerve expander with a saddle thereupon which guides or holds a nerve on an inflatable expansion member.

SUMMARY OF THE INVENTION

The general purpose of the present invention is to provide a low profile nerve expander with single or multiple saddles to guide or hold a nerve in position during surgical nerve expansion procedures.

According to one embodiment of the present invention, there is provided a low profile saddled nerve expander including a saddle like arrangement on an upper surface of an inflatable expansion member. The saddle, including a partial cylindrical shaped saddle trough between two parallel rounded trough top members, is affixed on a surface of an inflatable expansion member. The partial cylindrical shaped saddle trough accommodates nerve tissue, and keeps the tissue from slipping from the top surface of the inflatable expansion member. An optional strap provides for additional securement of a nerve tissue within the saddle trough and upon the upper surface area of the inflatable expansion member. Multiple saddles will be attached to the nerve expander when longer expanders are required.

A significant aspect and feature of the present invention is a low profile nerve expander for forced directional deployment of the expandable member.

Another significant aspect and feature of the present invention is one or more nerve saddles on a surface of an inflatable expansion member to prevent nerve slippage during a reconstructive surgical procedure.

Yet another significant aspect and feature of the present invention is a saddle using a partial cylindrically shaped trough between parallel rounded trough top members.

A further significant aspect and feature of the present invention is an optional strap over the saddle trough to assure engagement of a nerve within the saddle and on the upper surface area of the inflatable expansion member.

Still another significant aspect and feature of the present invention is a substantially rigid but malleable backing plate in the expandable member to enhance directionality of expansion and to assist in conforming the nerve expander to the underlying body structure.

And still another significant aspect and feature of the present invention is the use of an injection port to expand an inflatable expansion member of a nerve expander with a saddle thereupon.

Having thus described embodiments of the present invention, it is a principal object hereof to provide a nerve expander.

One object of the present invention is to provide an inflatable nerve expander with one or more nerve positioning saddles for prevention of nerve slippage from a surface of the inflatable expansion member.

Another object of the present invention is to provide a low profile inflatable nerve expander including a saddle and strap arrangement.

A further object of the present invention is a nerve expander with a substantially rigid but malleable backing for conformation to underlying surfaces.

Yet another object of the present invention is a nerve expander utilizing forced directional expansion of the expandable member.

A further object of the present invention is a nerve expander incorporating a self-sealing injection port for inflation of an inflatable expansion member with a positioning saddle thereupon.

BRIEF DESCRIPTION OF THE DRAWINGS

Other objects and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
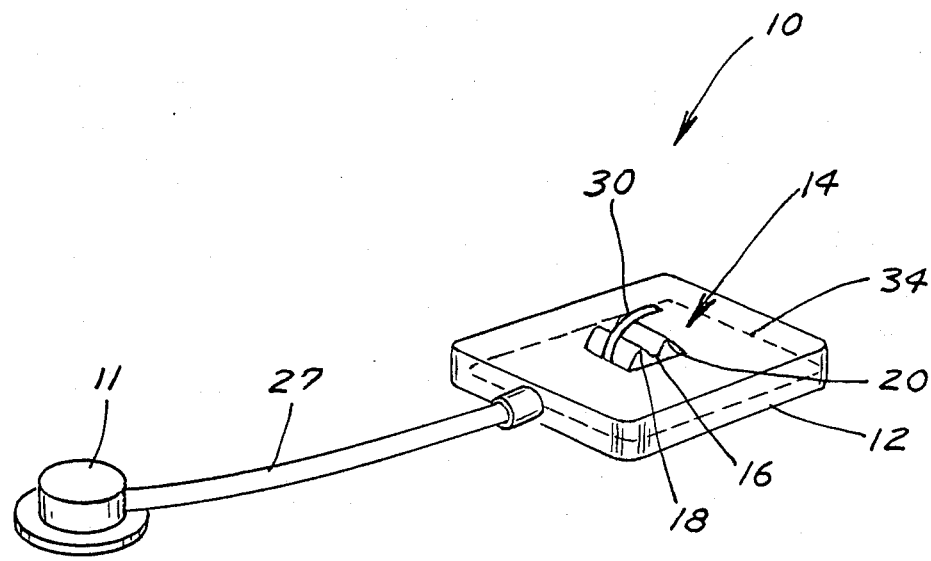
FIG. 1 illustrates a perspective view of a nerve expander.

FIG. 1 illustrates a perspective view of a nerve expander system 10 including a self-sealing injection port 11, a tube 27, an inflatable expansion member 12, and a configured nerve saddle 14 on an upper surface of the inflatable expansion member 12.

Figure 2:
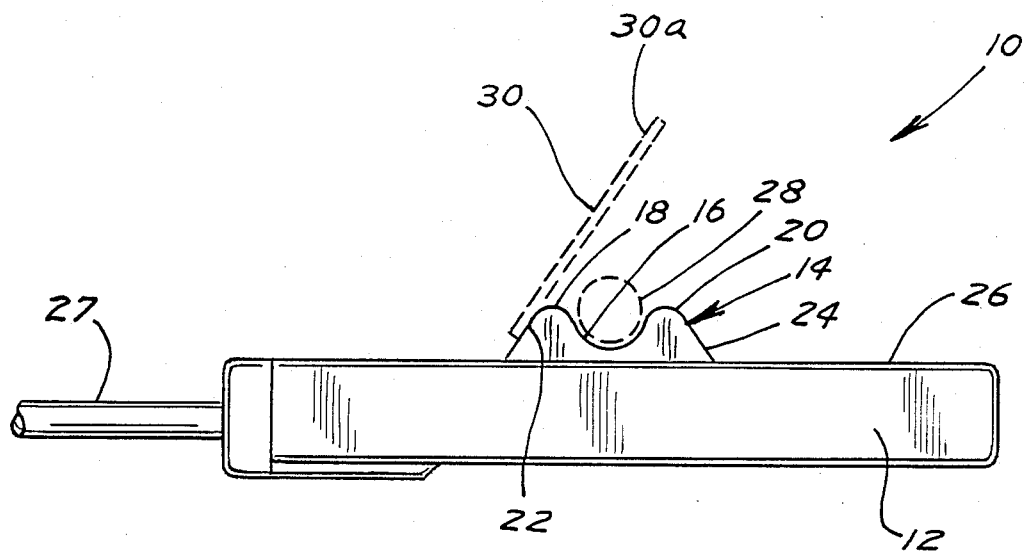
FIG. 2 illustrates a side elevation of a nerve expander, the present invention.

FIG. 2 illustrates a side elevational view of the nerve expander 10, the present invention, including the self-sealing injection port 11 and the inflatable expansion member 12. The nerve expander 10 also includes a single configured nerve saddle 14 of silicone or other suitable material which is molded or otherwise suitably affixed to inflatable expansion member 12, and includes a partial cylindrical shaped saddle trough 16 included between parallel rounded trough top members 18 and 20. Sloping outer walls 22 and 24 angle downwardly from the parallel rounded trough members 18 and 20 to meet the expander top surface 26 of the inflatable expansion member 12. Other edge members include radiused edges to inhibit any undue stress on the nerve which could be caused by sharper unradiused edges. The top portions of trough top members 18 and 20 are round in shape, and the outer walls 22 and 24 angle downwardly from the rounded trough top members 18 and 20 to present a smooth, nonirritating surface when placed subcutaneously beneath human tissue. The nerve expander 10, including nerve saddle 14, is placed under nerve tissue 28, shown in dashed lines. The nerve tissue 28 is then placed in the saddle trough 16. The inflatable expansion member 12 is then inflated through tube 27 by injection of a saline solution for sequential expansion of the nerve through the self-sealing injection port 11.

Figure 3:
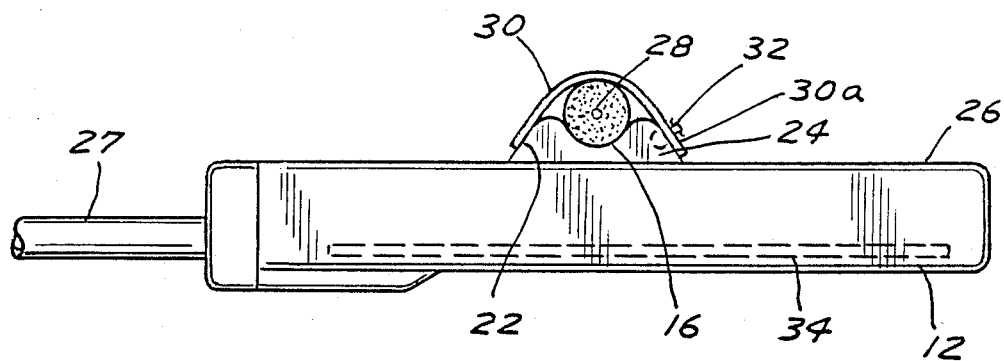
FIG. 3 illustrates a side elevation of a nerve expander of FIG. 1 including a nerve attached thereto.

FIG. 3 illustrates a side elevational view of the nerve expander utilizing an optional flexible and pliable nerve securement strap 30 of silicone or other suitable material shown in dashed lines in FIG. 2 where all numerals correspond to those elements previously described. Nerve securement strap 30 is mounted, molded to, or otherwise affixed to the outer wall 22. After placement of the nerve expander 10 beneath the nerve in the saddle trough 16 as previously described, nerve securement strap 30 is placed over the nerve tissue 28 and nerve saddle 14 where end 30a is secured by a suture 32 through the outer wall 24. In the alternative, end 30a could be attached to outer wall 24 by other suitable means such as a snap, glue, surgical velcro or other like securing devices. A malleable plate 34 is embedded in the lower regions of the inflatable expansion member 12.

Figure 4:
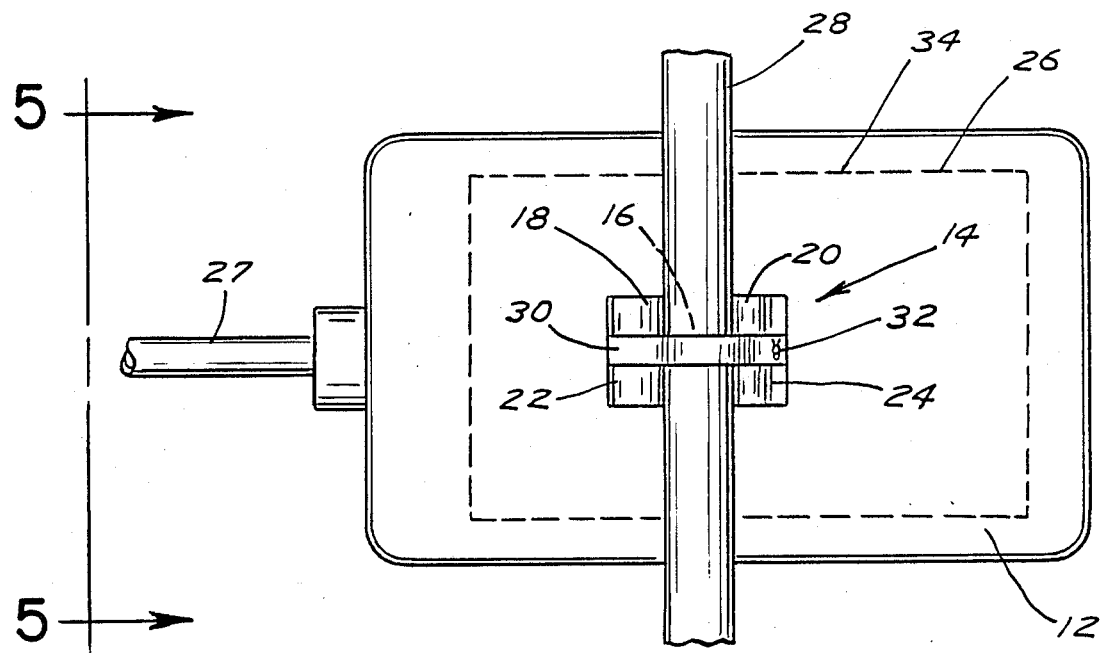
FIG. 4 illustrates a top view of the nerve expander of FIG. 3 including a nerve attached thereto.

FIG. 4 illustrates a top view of FIG. 3 where all numerals correspond to those elements previously described. Noted in particular is the securement of the nerve tissue 28 within the nerve saddle 14.

MODE OF OPERATION

Figure 5:
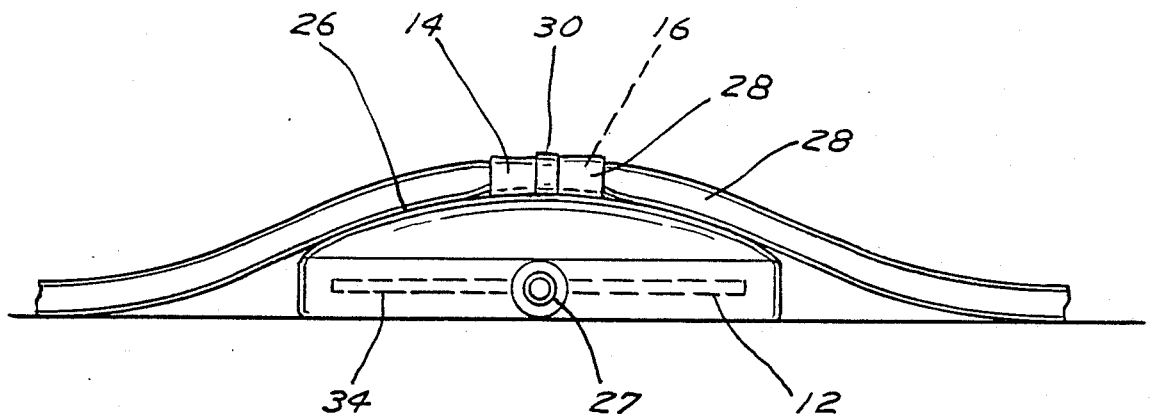
FIG. 5 illustrates an end view from lines 5—5 of FIG. 4 illustrating an inflated nerve expander.

FIG. 5, in conjunction with FIGS. 1-3, illustrates the mode of operation where all numerals correspond to those elements previously described. The nerve tissue 28 is placed in saddle trough 16 concurrently with the placement of the inflatable expansion member 12. The nerve expander 10 is subsequently and sequentially inflated by injection of a saline or other solution into the self-sealing injection port 11 of FIG. 1 and through the inflation tube 27 to lengthen the nerve tissue 28 by mild stretching of the nerve tissue 28 due to the interceding and expansion of the inflatable expansion member 12 between the nerve tissue 28 and body members below the nerve to facilitate direct reattachment at a later time.

After subcutaneous placement of the nerve expander 10, including the self-sealing injection port and tube 27 of FIG. 1, the surgical site is closed with the expander remaining in place. After the incision has settled, expansion may begin by sequentially injecting normal saline solution into the system through the self-sealing injection port 11 to expand the inflatable expansion member 12. During the expansion process, the nerve saddle 14 and the optional nerve securement strap 30, if desired, retain the nerve tissue 28 on the top area of the inflatable expansion member 12 to assure maximum lengthening of the nerve for the required amount of expansion.

When sufficient nerve tissue length is obtained, the nerve expander is surgically removed and direct reconstruction of the nerve tissue can be accomplished. The nerve tissue expansion may eliminate the need for graft material across a nerve gap.

The saddle trough 16 provides a channel or saddle for the nerve tissue 28 to rest in, and simultaneously provides for keeping the inflatable expansion member 12 in proper alignment beneath the nerve tissue 28 and preventing the nerve expander 10 from migrating out and from beneath the associated nerve fiber. Optional nerve securement strap 30, as illustrated, fits over the nerve tissue 28, and is used for positive containment and securement of the nerve tissue 28 within the saddle through 16 of the nerve saddle 14 to prevent the nerve from slipping out of the saddle 14 and off of expander top edge 26 of the inflatable expansion member 12 during the reconstructive period. The nerve saddle 14 can be lengthened along the axis of saddle trough 16 for additional support area along the nerve tissue 28. The saddle trough 16 presents a smooth and conforming surface to the nerve to reduce the chance of damage during the procedure. Forced directional low profile design is provided where the bottom of the expander remains substantially flat due to bottom reinforcement malleable plate 34. The optional malleable rigid stainless steel backing plate 34 or like backing member, illustrated in dashed lines, in the inflatable expansion member 12 can further enhance directionality and can improve the conformity of the inflatable expansion member 12 to the underlying body structure by bending the malleable plate 34 along body contours. When sufficient nerve length is attained, the device is surgically removed and reconstruction of the nerve tissue is accomplished.

DESCRIPTION OF THE ALTERNATIVE EMBODIMENTS

Figure 6:
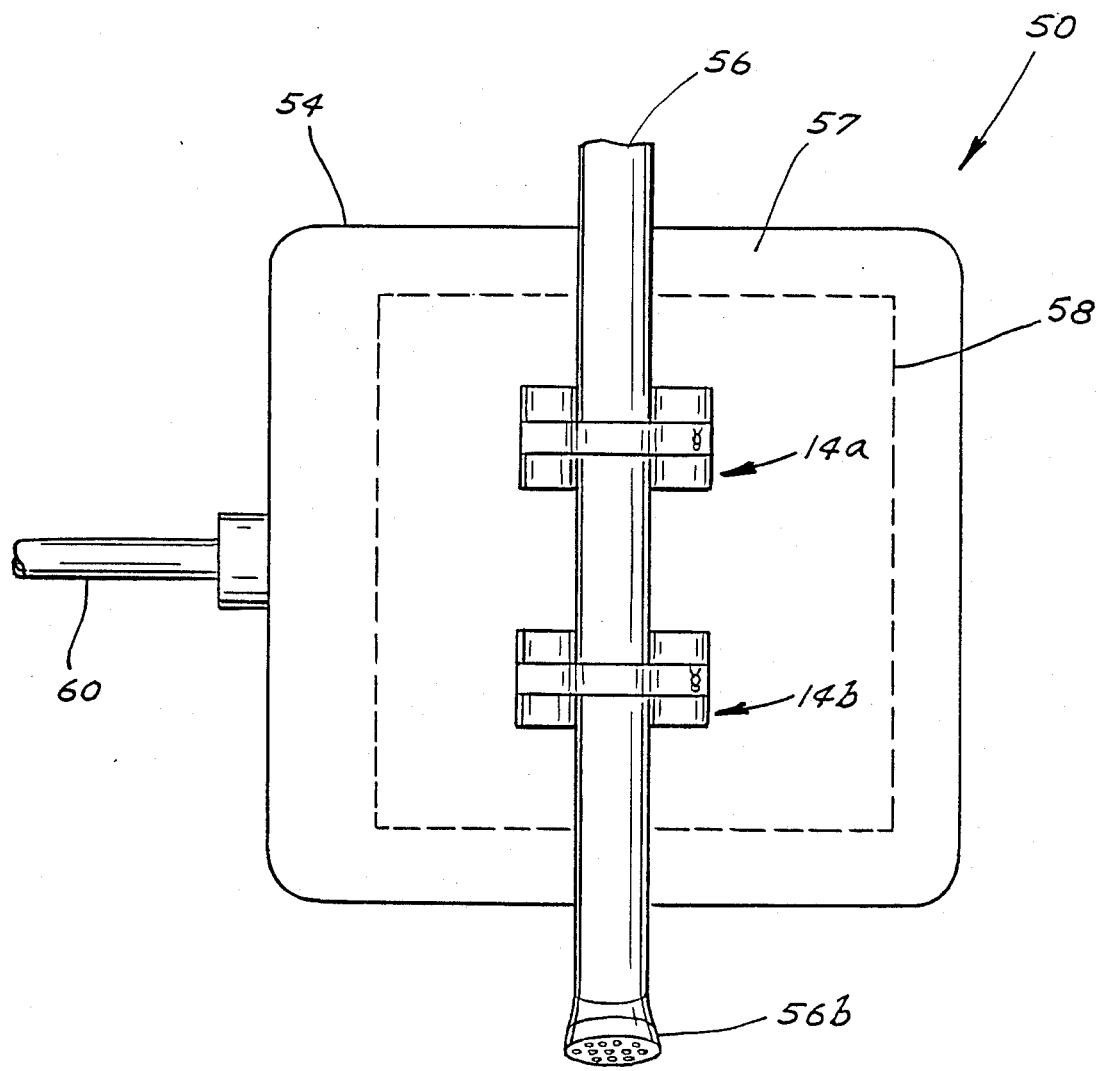
FIG. 6 illustrates a nerve expander with dual saddles.

FIG. 6 illustrates an alternative embodiment and top view of the nerve expander 50 with two similar nerve saddles 14a and 14b mounted on an upper surface 52 of an inflatable expansion member 54 for use when it is desired to obtain a greater degree of nerve expansion or stretch by supporting and engaging a nerve tissue 56 with a pair of saddles identical to saddle 14, as previously described and designated herein as saddles 14a and 14b, at two points along nerve tissue 56. Although two saddles 14a and 14b are illustrated, any desired number of saddles could be used and the number of saddles used shall not be construed as limiting to the scope and intent of the invention. A malleable rigid stainless steel backing plate 58 is embedded in the lower region of the inflatable expansion member 54. An inflation tube 60 connects to the inflatable expansion member for expansion of the expansion member 54 by injection of a saline or other solution through a self-sealing injection port 11 as illustrated in FIG. 1.

Figure 7:
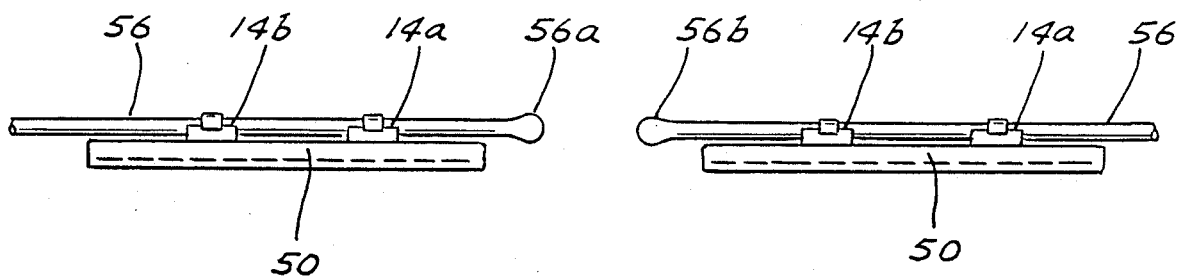
FIG. 7 illustrates severed nerve fibers engaged within dual saddle nerve expanders.

FIG. 7 illustrates a severed nerve 56, including a proximal neuroma nerve end 56a and a glioma nerve end 56b, each respectively engaged in saddles 14a and 14b of a similar nerve expander 50. The inflatable expansion member 54 is inflated as previously described to expand or stretch the severed nerve tissue 56 until sufficient length is obtained to bring the proximal neuroma nerve end 56a adjacent to the glioma nerve end 56b for surgical joining and reconstruction.

Various modifications can be made to the present invention without departing from the apparent scope thereof.

We claim:

1. An inflatable low profile nerve tissue expander comprising:
    a. an inflatable expansion member of substantially flat geometrical configuration for receiving fluid to expand said member, b. a self-sealing injection port with a connecting tube of a finite length connected to said inflatable expansion member for passing the fluid for inflating said member;
c. at least one saddle including a partially cylindrical shaped trough in said saddle positioned on a top surface of said inflatable expansion member; and,
d. means for securing a nerve in said saddle, said means including a nerve securement strap affixed to one side of said trough and securable to the other side of said trough whereby said saddle accommodates nerve tissue to capture said nerve tissue about the surface area of said saddle for lengthening said nerve tissue on expansion, and said inflatable injection port and said connecting tube are surgically placed under an individual's skin adjacent the nerve to be expanded.

2. Expander of claim 1 including two saddles spaced with respect to each other on said inflatable expansion member.

3. Expander of claim 1 including a substantially rigid and malleable backing in a back side of said inflatable expansion member.

* * * * *